US00PP09548P

United States Patent [19]

Kovacevich, Jr.

[11] Patent Number: Plant 9,548

[45] Date of Patent: May 14, 1996

[54] 'BEV'S RED' PEACH TREE

[76] Inventor: John J. Kovacevich, Jr., 4001 Pinehurst, Bakersfield, Calif. 93306

[21] Appl. No.: 317,041

[22] Filed: Aug. 22, 1994

[51] Int. Cl.[6] ..... A01H 5/00

[52] U.S. Cl. ..... Plt./43.1

[58] Field of Search ..... Plt./43.1

[56] References Cited

U.S. PATENT DOCUMENTS

P.P. 5,745 5/1986 Zaiger et al. ..... Plt./43.1

*Primary Examiner*—James R. Feyrer
*Attorney, Agent, or Firm*—Worrel & Worrel

[57] ABSTRACT

A new and distinct variety of peach tree which is somewhat remotely similar to the "Topcrest" peach tree of which it is mutation, but from which it is distinguished by producing fruit which are larger and more highly colored than the fruit of the "Topcrest" peach tree and which are mature for harvesting and shipment approximately two and one-half weeks after the fruit of the "Topcrest" peach tree.

1 Drawing Sheet

BACKGROUND OF THE NEW VARIETY

The present invention relates to a new and distinct variety of peach tree which will hereinafter be denominated varietally as "Bev's Red" and, more particularly, to a peach tree which produces fruit which are mature for commercial harvesting and shipment approximately May 15 to May 18 in the southern San Joaquin Valley of California and which are large sized, highly colored and of good quality.

The development of new varieties of fruit trees is a continuing and necessarily painstaking process. The commercially significant attributes and general quality of tree fruit available on the market continues to improve as the result of the discovery and development of new varieties of fruit trees. As a consequence, varieties which were once considered superior may be surpassed in a very few years by new varieties with greater commercial appeal. Thus, in an effort to keep pace with competitors, many of those within the industry aggressively seek new varieties of superior character, particularly as to those criteria which the industry deems most important. Without such efforts, there is a risk of not remaining competitive in the marketplace.

However, the selection of superior fruit tree varieties from among a myriad of candidates requires patient observation over many years. A new variety which is a descendant of an existing, commercially successful variety may be an attractive candidate. Nonetheless, frequently such new varieties lack certain characteristics required for commercial success. It is rare to find such a new variety which exceeds the characteristics of an illustrious parent in a multiplicity of commercially significant criteria. The new variety of the present invention is believed to be such a descendant.

ORIGIN AND ASEXUAL REPRODUCTION OF THE NEW VARIETY

The variety of peach tree of the present invention was discovered in 1992 by the inventor in his orchard which is located near Arvin in the southern San Joaquin Valley of California. The invention discovered the new variety as a mutation of the "Topcrest" peach tree. The orchard was originally planted as "Fairlane" peach trees in 1987. These trees were grafted to "Topcrest" peach trees in 1988 . The applicant asexually reproduced the new variety in February, 1993 by grafting scions taken from the sport on to a "Topcrest" peach tree and a "Queencrest" peach tree in the same orchard. The invention observed the asexually reproduced grafts of the new variety and the fruit produced thereby and found them in all respects to be identical to the parent.

SUMMARY OF THE NEW VARIETY

The "Bev's Red" peach tree is characterized as to novelty by producing large, semi-freestone fruit which are of very high coloration. The fruit of the new variety are ripe for commercial harvesting and shipment approximately May 15 to May 18 in the southern San Joaquin Valley of California, or about two and one-half weeks after the fruit of the "Topcrest" peach tree of which it is a mutation. The fruit of the new variety is further distinguishable from that of the "Topcrest" peach tree by being consistently larger in size and more highly colored, having a blush coloration varying from light to darker red extending over seventy-five percent (75%) to ninety percent (90%) of the surface area thereof.

BRIEF DESCRIPTION OF THE DRAWING

The accompanying drawing is a color photograph showing fruit of the new variety including a first in side elevation showing the suture thereof; a second showing the base end; a third sectioned to show the flesh thereof; a fourth showing the apex end; and a fifth in side elevation; a stone of the new variety; and foliage typical of the new variety of peach tree.

DETAILED DESCRIPTION

Referring more specifically to the pomological details of this new and distinct variety of peach tree, the following has been observed under the ecological conditions prevailing at the orchard of origin which is located in Arvin in the southern San Joaquin Valley of California. All major color code designations are by reference to the *Dictionary of Color*, by Maerz and Paul, First Edition, 1930. Common color designations are occasionally employed to indicate color.

TREE

Generally: Tree is hardy under climatic conditions typical for the southern San Joaquin Valley of California.

*Size.*—Trained to a standard vase shape and has from 76.2 cm (30 inches) to 121.92 cm (48 inches) of growth in the upper portion of the canopy prior to pruning.
*Vigor.*—Vigorous.
*Form.*—Upright to upright-spreading.
*Productivity.*—Productive.
*Regularity of bearing.*—Regular.

Trunk:
*Size.*—Medium thickness.
*Surface texture.*—Relatively rough with substantial papery scarfskin.
*Color.*—Brownish-grey (15-E-11 New Bronze).
*Lenticels — Numbers.*—Numerous large oval lenticles present throughout the trunk surface.
*Lenticels — Size.*—Large.

Branches:
*Size.*—Medium thickness.
*Surface texture.*—Medium.
*Color — One year or older wood.*—Medium brown (7 -H-11 Rustic Brown).
*Color — Immature branches.*—Light green (19-I-4) with most exposed surfaces tinged with red pigmentation.

LEAVES

Size:
*Generally.*—Medium. Leaf measurements were taken from leaves growing near midpoint on vigorous, upright current season's shoots.
*Average length.*—15.2 mm (0.5984 inches) to 16.7 mm (0.6575 inches).
*Average width.*—13.9 mm (0.5472 inches) to 14.2 mm (0.5591 inches).

Form: Lanceolate. Leaf apices are acuminate. The apices are usually slightly twisted sideways and reflexed downwards.

Color:
*Upwardly disposed surface.*—Dark green (16-L-1).
*Downwardly disposed surface.*—Lighter grey-green (21-K- 5 Biscay Green).

Marginal form:
*Generally.*—Crenate with large, low, broad crenations. Occasionally the crenations are double, especially near the mid-margin.

Leaf margin: Usually slightly undulate.

Glandular characteristics: The glands are medium in size and most frequently reniform in form. From 2 to 5 glands can be present along the basal margin of the leaf blade. These glands are always reniform. Occasionally an additional 1 to 2 glands can be present on the petiole at the juncture with the base of the leaf blade. These glands are occasionally stalked and are most often reniform, but occasional globose variants can be present. Gland position is variable, most often alternate, but opposite pairs can occasionally be present.

Glands:
*Color.*—Bright, shiny green (19-L-2 Javel Green) when young, becoming somewhat darker with age.

Petiole:
*Size.*—Average.
*Length.*—10 mm (0.3937 inches) to 11 mm (0.4331 inches).
*Thickness.*—Average 2.0 mm (0.0787 inches )
*Color.*—Pale green (20-J-5 Absinthe Green).

Stipules: Early deciduous.
*Size.*—Relatively small.
*Length.*—5 mm (0.1969 inches) to 6 mm (0.2362 inches).
*Form.*—Lanceolate with serrate margins.
*Color.*—Light green (19-K-3 Chrysolite Green) becoming darker and deteriorating with age.

FLOWERS

Flower buds: Buds are slightly appressed to the bearing stem. Bud scale surfaces are highly pubescent with moderately long, greyish pubescence. The buds are hardy under climatic conditions typical for the southern San Joaquin Valley of California. This floral description was developed in early March of 1993 after a chilling season which could be characterized as below average in accumulation of chilling hours (number of hours at or below 45 degrees Fahrenheit from mid-November to mid-February).
*Size.*—Average.
*Form.*—Conic.

Flower bud scales:
*Color.*—Grey-brown (15-C-6 Grey #31).

Flowers:
*Generally.*—Large and of the "showy" type.

Date of bloom: Mar. 3, 1993. Slightly late in relation to other peach cultivars grown in the Arvin, Calif. region.

Bloom quantity: Amount of bloom developed in 1993 was average. One to two flower buds are present per node, most frequently 2.

Size:
*Diameter.*—Fully expanded, ranges from 33 mm (1.2992 inches) to 37 mm (1.4567 inches).
*Size.*—Relatively large.
*Length.*—13 mm (0.7480 inches (to 22 mm (0.8661 inches).
*Width.*—15 mm (0.5906 inches) to 18 mm (0.7087 inches).
*Number.*—Five.
*Form.*—Varies from oval to slightly obovate.
*Color.*—When young, a light pink (1-E-7 Pink 190 5) with darker rose (1-H-3) coloration basally and on the petal claw. The petals become darker in color with age. The petal color of the new variety is more deep rose than the original "Topcrest" peach tree, especially in the basal area.
*Claw.*—Relatively short 1.0 mm (0.0394 inches) to 1.25 mm (0.0492 inches), but broad 1.0 mm (0.0394 inches).
*Claw — Form.*—Truncate.
*Margin.*—Undulate with short crinkled undulations.
*Apex.*—Variable, from broadly rounded to more domed.
*Length.*—Average 2.0 mm (0.0787 inches).
*Thickness.*—1.5 mm (0.0591 inches).
*Color.*—Bright glossy green (20-L-3) Certosa Green).
*Surface.*—Glabrous.

Nectaries:
*Color.*—Bright orange (11-K-12), becoming darker and duller with age.

Calyx:
*Surface.*—Glabrous.
*Color.*—Maroon (7-H-5 Aubusson).

Sepals:
*Size.*—Medium to large.
*Form.*—Ovate.
*Surface.*—Pubescent with a long woolly pubescence.
*Color.*—Maroon (7-H-4) with occasional green hues near the margins.

Anthers:

*Size.*—Average.

*Color.*—Red (3-K-11 Flash Red) dorsally and light tan (11-J-6 Honeysweet) ventrally with red (3-K-11 Flash Red) margins. Pollen is abundant and is of a yellow-gold (9-L-4 Sunflower) coloration.

Stamens:

*Length.*—Longer in length than the pistil. 11 mm (0.4331 inches) to 18 mm (0.7087 inches).

Filament:

*Color.*—Light pink (1-C-7 Pink #2) when young, becoming a deep rose (2-D-4) with maturity.

Pistil:

*Length.*—Ranges from 15 mm (0.5906 inches) to 17 mm (0.6693 inches) including ovary.

*Color.*—Pale green-yellow (18-E-2) with some red shading present as the flower matures and the petals drop.

*Surface.*—Pubescent.

FRUIT

Maturity when described: Ripe for commercial harvesting and shipment approximately May 15 to May 18 in 1992 near Arvin in the southern San Joaquin Valley of California. In 1995, the fruit of the new variety of the present invention reached maturity on May 12. In contrast, the fruit of the "Topcrest" peach tree reached maturity in 1995 on April 25. These comparisons were made in the orchard of origin near Arvin, in the southern San Joaquin Valley of California.

Size:

*Generally.*—Medium to Large for fruit of the general maturity date. Uniform.

*Average diameter in the axial plane.*—65 mm (2.559 inches) to 68 mm (2.677 inches).

*Average diameter in the cheek plane.*—67 mm ( 2.638 inches) 74 mm (2.913 inches).

*Average diameter in the suture plane.*—69 mm (2.717 inches) to 78 mm (3.071 inches).

Form:

*Uniformity.*—Variable in lateral aspect from oval to slightly oblate. The fruit is most frequently oval in apical aspect.

*Symmetry.*—Usually asymmetrical with one side of the fruit larger than the other. The fruit of the new variety is generally less symmetrical than the fruit of the "Top Crest" peach tree.

Suture:

*Generally.*—The suture is a relatively thin, somewhat discontinuous line from base to apex. A slight amount of stitching is present along the suture, most frequently located near mid-suture.

*Color.*—Variable. At times the coloration matches the surrounding blush color. Other times the suture is yellow (9-I-4).

*Width.*—1.0 mm (0.0394 inches) to 1.5 mm (0.0591 inches).

Ventral surface:

*Generally.*—Smooth with only slight lipping.

Stem cavity:

Generally.—Relatively small.

*Width.*—124 mm (0.9449 inches) to 29 mm (1.1417 inches).

*Depth.*—Medium, 12 mm (0.4724 inches) to 14 mm (0.5512 inches).

*Length.*—32 mm (1.260 inches) to 38 mm (1.496 inches).

*Shape.*—Cavity outline is oval and quite regular. Slight folding of the suture occurs with the cavity basin.

Stem:

*Length.*—Medium, 9 mm (0.3543 inches) to 12 mm (0.4724 inches).

*Thickness.*—Ranges from 3.5 mm (0.1378 inches) to 4.0 mm (0.1575 inches).

*Color.*—Varies from an olive green (21-L-2 Moss Green) to a brown (15-L-10 Whippet Brown).

Base:

*Form.*—Variable from rounded to slightly truncate. The base angle is very oblique to the fruit axis.

Apex:

*Form.*—Variable from rounded to moderately pointed. Most frequently a strong depression is present on the ventral suture side of the pistil point with a slightly less strong depression present on the dorsal suture side.

Pistil point: Variable from apical to slightly oblique.

Skin:

*Thickness.*—Average.

*Texture.*—Pubescent with a short, fine, greyish pubescence. The skin is slightly acidic and is tenacious to the flesh at commercial maturity.

*Tendency to crack.*—None observed.

*Color.*—Coloration is from 75 to 90 percent red blushed. Blush form varies from washed to finely striped to dappled.

*Blush color.*—Variable from light red (4-I-11 Carnelain Red) to a darker red (5-K-11 Moroccan Red), which especially involves the dappled and striped areas, to an even darker garnet red (5-K-12 Autumn Glory) over the darkest areas.

*Ground color.*—Present on 10 to 20 percent of the fruit surface and is a medium yellow (10-K-4 Narcissus Yellow). This ground color yellow is most often present over the suture area.

*Flesh color.*—Bright yellow (10-J-5 Corn Yellow) and is relatively uniform throughout.

*Juice production.*—Juicy.

*Flavor.*—Sweet and mildly acid, but with good balance.

*Aroma.*—Moderately aromatic, pleasant.

*Texture.*—Firm and crisp at commercial maturity, becoming juicy with afteripening.

*Fibers.*—Numbers — An average number of medium length, light colored, tender fibers are present in the flesh.

*Ripening.*—Evenly.

*Eating quality.*—Very good, especially for the fruit's early season of maturity.

Stone:

*Attachment.*—Semi-freestone. Tightly attached at commercial maturity, becoming more free with full maturity.

*Fibers.*—Numbers — Numerous medium length fibers are present, attached along both the ventral and dorsal sutures.

*Size.*—Medium.

*Size — Length.*—Ranges from 35 mm (1.3780 inches) to 38 mm (1.4961 inches).

*Size — Width.*—24 mm (0.9449 inches) to 27 mm (1.0630 inches).

*Size — Thickness.*—20 mm (0.7874 inches) to 22 mm (0.8661 inches).

*Form.*—Generally — Variable from ovate to oval.

*Apex.*—Shape — Acute with an acute tip.

*Color.*—Dry — Uniform light tan (10-H-5).

*Base.*—Shape — Variable, most frequently moderately truncate. Base angle is also variable, most frequently slightly oblique to the fruit axis but at times nearly at a right angle to the axis.

*Sides.*—Generally — Usually distinctly unequal.

*Surface.*—Relatively coarse, deeply pitted and grooved. Both oval and globose pits occur over the lateral surfaces. Large, deep grooves are present most frequently over the apical shoulders and along the ventral suture.

*Hilum.*—Moderately large and oval in form, with a moderately thick, finely grooved collar.

*Ventral edge.*—Relatively broad, from 6 mm (0.2362 inches) to 10 mm (0.3937 inches) wide at mid-suture. The ventral edge is made up of a multiple band of coalesced low wings, converging apically, and most prominent from mid-stone to the base. The wings protrude from 4 mm (0.1575 inches) to 6 mm (0.2362 inches).

*Dorsal edge.*—Characterized by a distinct and moderately deep groove, extending from the base to the apex of the stone. The groove becomes more shallow over the apical shoulder. The groove is flanked on each side by a relatively narrow, high ridge, most prominent at mid-stone.

*Ridges.*—Usually cross-cut in several places along the suture by grooves.

*Tendency to split.*—No specific tendency to split has been observed.

Use: Fresh market.

Keeping quality: Good.

Although the new variety of peach tree possesses the described characteristics noted above as a result of the growing conditions prevailing near Arvin in the southern San Joaquin Valley of California, it is to be understood that variations of the usual magnitude and characteristics incident to changes in growing conditions, irrigation, fertilization, pruning, pest control, seasonal climatic variation and the like are to be expected.

Having thus described and illustrated my new variety of peach tree, what I claim as new and desire to be secured by Plant Letters Patent is:

1. A new and distinct variety of peach tree substantially as illustrated and described and which is somewhat remotely similar to the "Topcrest" peach tree from which it was derived, but from which it is distinguished by producing larger, more highly colored fruit which are mature for commercial harvesting and shipment approximately May 15 to May 18 in the San Joaquin Valley of California, or about two and one-half weeks after the fruit of the "Topcrest" peach tree.

* * * * *

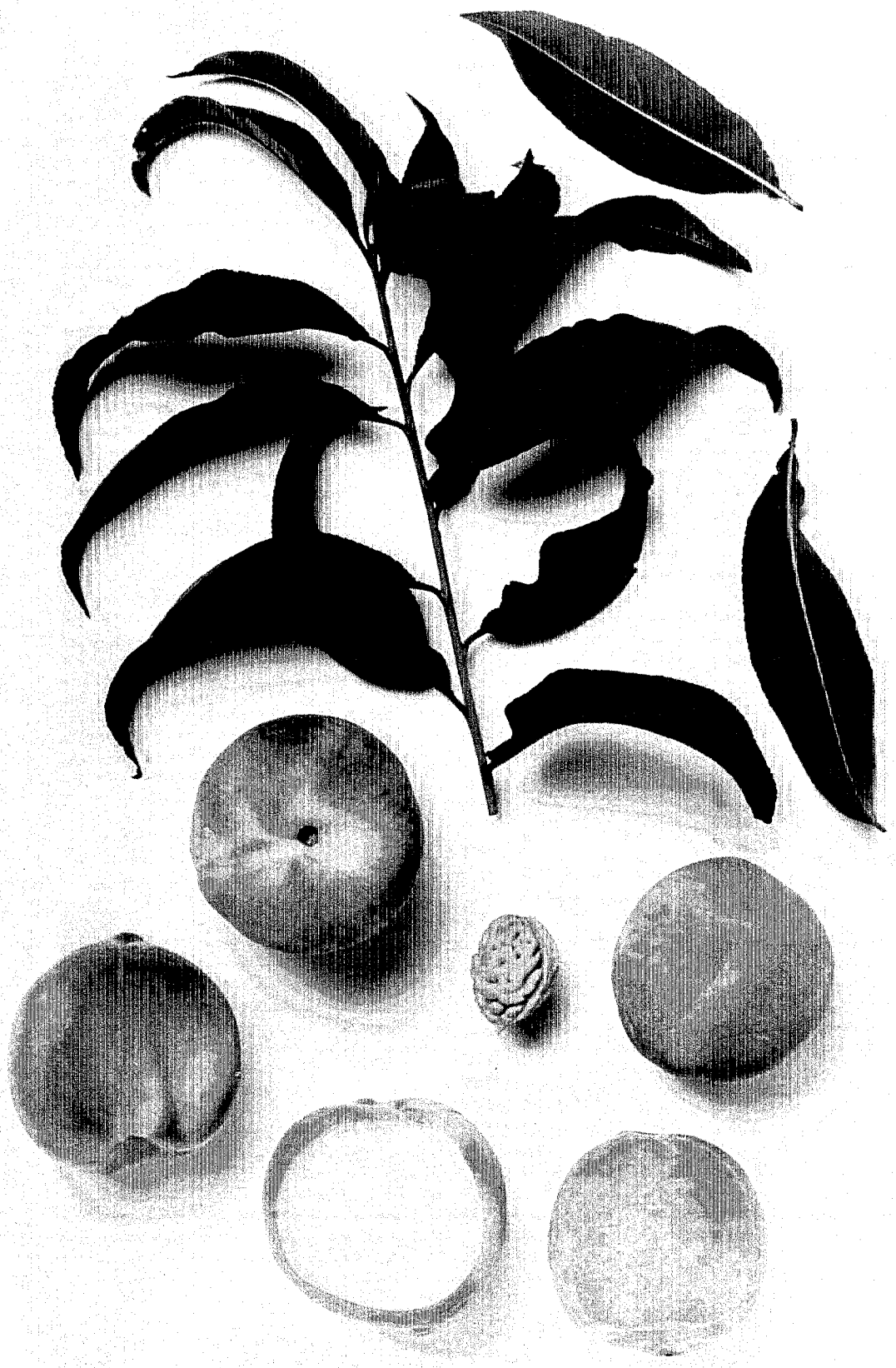

UNITED STATES PATENT AND TRADEMARK OFFICE

CERTIFICATE OF CORRECTION

PATENT NO. : PP 9,548

DATED : May 14, 1996

INVENTOR(S) : JOHN J. KOVACEVICH, JR.

It is certified that error appears in the above-identified patent and that said Letters Patent is hereby corrected as shown below:

Column 4, line 40, delete "190 5" and substitute ---#5---.

Column 6, line 29, delete "Carnelain" and substitute ---Carnelian---.

Signed and Sealed this

Eighth Day of October, 1996

*Attest:*

Bruce Lehman

BRUCE LEHMAN

*Attesting Officer*

*Commissioner of Patents and Trademarks*